US008758747B2

(12) United States Patent
Kallmeyer et al.

(10) Patent No.: US 8,758,747 B2
(45) Date of Patent: Jun. 24, 2014

(54) STABLE LYOPHILIZED PHARMACEUTICAL PREPARATIONS OF MONOCLONAL OR POLYCLONAL ANTIBODIES

(75) Inventors: Georg Kallmeyer, Mannheim (DE); Gerhard Winter, Dossenheim (DE); Christian Klessen, Lauterecken (DE); Heinrich Woog, Laudenbach (DE)

(73) Assignee: Roche Diagnostics GmbH, Mannheim (DE)

( * ) Notice: Subject to any disclaimer, the term of this patent is extended or adjusted under 35 U.S.C. 154(b) by 664 days.

(21) Appl. No.: 12/180,794

(22) Filed: Jul. 28, 2008

(65) Prior Publication Data

US 2008/0286280 A1   Nov. 20, 2008

Related U.S. Application Data

(63) Continuation of application No. 09/308,223, filed as application No. PCT/EP97/06452 on Nov. 19, 1997, now abandoned.

(30) Foreign Application Priority Data

Nov. 19, 1996 (EP) .................................... 96118489

(51) Int. Cl.
*A61K 39/395* (2006.01)
*C07K 16/00* (2006.01)
*C12P 21/08* (2006.01)
*A61K 9/19* (2006.01)

(52) U.S. Cl.
CPC .............. *A61K 39/395* (2013.01); *C07K 16/00* (2013.01); *A61K 9/19* (2013.01)
USPC .................. 424/130.1; 424/141.1; 530/387.1; 530/388.1

(58) Field of Classification Search
None
See application file for complete search history.

(56) References Cited

U.S. PATENT DOCUMENTS

| 4,165,370 A | 8/1979 | Coval |
| 4,384,993 A | 5/1983 | Sato et al. |
| 4,597,966 A | 7/1986 | Zolton et al. |
| 5,096,885 A | 3/1992 | Pearlman et al. |
| 5,410,025 A | 4/1995 | Moller et al. |
| 5,440,021 A | 8/1995 | Chuntharapai et al. |
| 5,608,038 A | 3/1997 | Eibl et al. |
| 5,750,142 A | 5/1998 | Friedman et al. |
| 5,763,409 A | 6/1998 | Bayol et al. |
| 5,908,826 A | 6/1999 | Fukuda et al. |
| 5,919,443 A * | 7/1999 | Michaelis et al. ......... 424/85.1 |
| 6,204,036 B1 | 3/2001 | Metzner et al. |
| 6,267,958 B1 * | 7/2001 | Andya et al. ............. 424/130.1 |
| 2001/0055617 A1 * | 12/2001 | Mattern et al. ............ 424/489 |
| 2008/0286280 A1 | 11/2008 | Kallmeyer et al. |

FOREIGN PATENT DOCUMENTS

| CZ | 247484 B1 | 5/1986 |
| EP | 0 196 761 A2 | 10/1986 |
| EP | 0597101 A1 | 5/1994 |
| EP | 0 689 843 A1 | 1/1996 |
| WO | 8400890 A1 | 3/1984 |
| WO | 89/11297 | 3/1989 |
| WO | 8907945 A1 | 9/1989 |
| WO | WO 89/09614 A1 | 10/1989 |
| WO | WO 92/01442 A1 | 2/1992 |
| WO | 93/05799 A1 | 4/1993 |
| WO | WO 94/07510 A1 | 4/1994 |
| WO | WO 94/14465 A1 | 7/1994 |
| WO | WO 95/07108 A2 | 3/1995 |
| WO | 97/04801 A1 | 2/1997 |
| WO | WO 97/04801 A1 | 2/1997 |
| WO | WO 97/15288 A2 * | 5/1997 | ............... A61K 9/14 |
| WO | WO 98/22136 * | 5/1998 | ............ A61K 39/395 |

OTHER PUBLICATIONS

Mannose (PubChem Compound, Aug. 3, 2011).*
Manning et al., "Stability of Protein Pharmaceuticals", Pharmaceutical Research, vol. 6, No. 11, 1989, pp. 903-918.
Hanson et al., "Introduction of Formulation of Protein Pharmaceuticals", Chaper 7 in Stability of Protein Pharmaceuticals, Part B in Vivo Pathways of Degradation and Stategies for Protein Stabilization, 1992.
Nema et al., "Freeze-Thaw Studies of a Model Protein, Lactate Dehydrogenase, in the Presence of Cryoprotectants", J Parent.Sci. Technol., 47, S. 76-83 (1993).
Inventory of Ingredients used in cosmetic products, : SO, Sep. 8, 2003.
Bioplasma FDP lyophilised powder for IV infusion. Package insert, Jan. 2002.
Hora et al., "Development of a lyophilized formulation of interleukin-2", Develop. Biol. Standard, vol. 74, pp. 295-306 (Karger, Basel, 1991).
Jablonowska et al., "Prevention of recurrent spontaneous abortion by intravenous immunoglobulin: a double-blind placebo-controlled study", Human Reproduction, vol. 14, No. 3, pp. 838-841, 1999.
Wang et al., "Parenteral Formulations of Proteins and Peptides: Stability and Stabilizers", Journal of Parenteral Science & Technology, 42, 1988, S4-S26.
Carpenter et al., "Interactions of stabilizing additives with proteins during freeze-thawing and freeze-drying", Develop. Biol. Standard, vol. 74, pp. 225-239 (1991).
Opposition in European Patent No. 0941121B, Jun. 20, 2005.
Draber et al., "Stability of monoclonal IgM antibodies freeze-dried in the presence of trehalose", Journal of Immunological Methods, vol. 181, pp. 37-43 (1995).
Arizono et al., Arzneimittelforschung, vol. 44, No. 7, 1994 (abstract only).

(Continued)

*Primary Examiner* — Peter J Reddig
(74) *Attorney, Agent, or Firm* — Rothwell, Figg, Ernst & Manbeck, P.C.

(57) ABSTRACT

The invention concerns lyophilized pharmaceutical preparations of monoclonal or polyclonal antibodies which contain a sugar or an amino sugar, an amino acid and a surfactant as stabilizers. In addition the invention concerns a process for the production of this stable lyophilizate as well as the use of a sugar or amino sugar, an amino acid and a surfactant as stabilizers for therapeutic or diagnostic agents containing antibodies.

3 Claims, No Drawings

(56) References Cited

OTHER PUBLICATIONS

Kishimoto et al., "Identification of a human peripheral lymph node homing receptor: A rapidly down-regulated adhesion molecule",Proc. Natl. Acad. Sci., vol. 87, pp. 2244-2248, Mar. 1990.
Shulman et al., "An antibody reactive with domain 4 of the platelet-derived growth factor β receptor allows BB binding while inhibiting proliferation by impairing receptor dimerization", The Journal of Bilogical Chemistry, vol. 272, No. 28, Issue of Jul. 11, pp. 17400-17404, 1997.
Wikipedia Extract—Histidin—4 pages, Mar. 29, 2011.
Northover, "Effect of anti-inflammatory drugs on the binding of calcium to cellular membranes in various human and guinea-pig tissues", Br. J. Pharmac (1973), 48, pp. 496-504.
Frokjaer et al., "Pharmaceutical Formulation Develoment of Peptides and Proteins", Taylor & Francis Limited (2000), 9 pages.
McFarlane, "Labelling of Plasma Proteins with Radioactive Iodine", Biochem J., 62 (1956), 135-143.
Abelow, Benjamin, Understanding Acid-Base, Chapter 1, Review of Fundamentals, 5 pages, 1998.
Aulton, Michael E., "Pharmaceutics: The Science of Dosage Form Design", 1988, Chapter 3, pp. 38-49.
Aulton, Michael E., "Pharmaceutics: The Science of Dosage Form Design", 1988, Chapter 4, pp. 254-268.
Cardy et al., "Techniques for Starch Gel Electrophoresis of Enzymes from Maiz (*Zea mays* L.)", Institute of Statistics Mimeograph Series No. 1317, Jun. 1981, pp. 1-31.
Doonan, Shawn, "Making and Changing Buffers", Methods in Molecular Biology, vol. 59, pp. 103-107, 1996.
Fifis et al., "Purification of 3-Phosphoglycerate Kinase from Diverse Sources by Affinity Elution Chromatography", Biochem J. (1978), 176, pp. 311-319.
Linskens et al, "Modern Method of Plant Analysis", New Series vol. 14, pp. 64-93, 1992.
Stricker, Dr. H., "Pharmazeutisch angewandte physikalisch-chemische Grundlagen", Physikalische Pharmazie, 1987, pp. 409-411.
Taylor, "The Classification of Amino Acid Conservation", J. Theor. Biol., (1986), 119, pp. 205-218.
Watersolve International, LLC, "Preparation of Pharmaceutical Waters", http://www.watersolve.com, Sep. 2006, pp. 1-9.
Daugherty, "Formulation and delivery issues for monoclonal antibody therapeutics", Advanced Drug Delivery Reviews, 58, (2006), p. 686-706.
Article from EMEA, Scientific Discussion for the Approval of Herceptin, 2005, 42 pages.

* cited by examiner

STABLE LYOPHILIZED PHARMACEUTICAL PREPARATIONS OF MONOCLONAL OR POLYCLONAL ANTIBODIES

The invention concerns lyophilized pharmaceutical preparations of monoclonal or polyclonal antibodies which contain a sugar or amino sugar, an amino acid and a surfactant as stabilizer. In addition the invention concerns a process for the production of these stable lyophilisates as well as the use of a sugar or amino sugar, an amino acid and a surfactant as stabilizers of therapeutic or diagnostic agents containing antibodies.

The production of immunoglobulins in particular monoclonal and polyclonal antibodies, for therapeutic and diagnostic purposes is nowadays of major and continuously increasing importance.

The use of antibodies as pharmacological agents has been already known for a long time and comprises numerous applications. Hence antibodies have been for example used successfully for tetanus prophylaxis, to combat pathogenic microorganisms or to neutralize their toxins and also for poisoning by snake venoms.

If the antigen involved in the disease mechanism has been identified, which is the case for numerous infectious and some oncological indications for antibody therapy, one utilizes the specificity of the antibodies for the therapy.

In clinical and preclinical studies antibodies are presently used to lower the cholesterol level, to influence the angiotensin/renin system and in autoimmune diseases such as for example lupus, autoimmune encephalitis, multiple sclerosis, polyarthritis and autoimmune myasthenia gravis.

Additionally of major therapeutic importance is their application to counteract intoxications by low molecular substances such as e.g. the Fab fragments of anti-digoxin antibodies when used for intoxications by digoxin or the cardiac glycosides digitoxin and ouabain. Moreover antibodies are used in the diagnostic field to identify, purify and determine the content of proteins.

Genetic engineering which revolutionized the production of monoclonal antibodies in cell cultures in the second half of the 70's and in the 80's has greatly advanced the preparation of antibodies.

In order to fulfil these diverse applications it is necessary to have pharmaceutical preparations of monoclonal and polyclonal antibodies that are stable on storage. There are a number of publications relating to liquid formulations or lyophilisates of special antibodies. Thus for example liquid formulations of antibodies are described in EP 0 280 358, EP 0 170 983, WO 89/11298, EP 0 352 500 and JP 63088197.

According to EP 0 280 358 dextran is added to the antibody solution to stabilize it towards certain hormones by which means it was possible to achieve a stability of over nine months. According to EP 0 170 983 hydrolysed ovalbumin is added to stabilize a thermolabile monoclonal antibody when heated and as a result the antibody could still be used after storage at 45° C. for 7 days. Polyhydroxy alcohols (e.g. glycerol, inositol, polyvinyl alcohol) or sugars (e.g. sucrose and glucose) or glycitols (e.g. sorbitol, mannitol) are known from JP 63088197 as further stabilizers for liquid formulations. WO 89/11298 demonstrates the use of maltose in a phosphate buffer containing sodium chloride as a further method for the liquid stabilization of monoclonal antibodies. EP 0 352 500 describes polyethylene glycol 4000 and 3-propiolactone for the liquid stabilization of monoclonal antibodies.

However, in general liquid formulations are not an optimal solution due to storage stability since the proteins or aggregates thereof may precipitate in time during storage, at increased temperatures, when transported through different climatic zones or by improper storage (e.g. interruptions in the cool chain) and the solutions may thus have a reduced protein content and become turbid. Hence, a problem-free use of the solutions cannot be guaranteed in these cases.

In contrast in the case of a lyophilisate formulation the removal of water minimizes the formation of degradation products (e.g. by deamidation and hydrolysis) and aggregate formation. The residual content of water (bound water) can contribute to the stability particularly in the presence of sugars (Hsu et al. Dev. Biol. Stand. 1991, 74: 255-267 and Pikal et al., Dev. Biol. Stand. 1991, 74: 21-27).

Lyophilisate formulations with special antibodies as active substances are also known from the literature but they do not give consistent advice about the problem of stabilization. Hence in WO 93/00807 the stabilization of biomaterials is described such as human proteins, growth hormones, interleukins, interferons, enzymes and also monoclonal and polyclonal antibodies by a two component system consisting of cryoprotective agents (e.g. polyethylene glycols) and a compound which can form hydrogen bridges with proteins. However, a disadvantage of these preparations is that the addition of high molecular compounds such as polyethylene glycols can lead to an accumulation in the body with potentially toxic side-effects if there is no biodegradation. Furthermore, as is well-known, polymers can act as antigens depending on their molar mass.

Lyophilisates of a monoclonal antibody that is labile when frozen are stabilized for one year according to JP 60146833 by the addition of albumin (human, horse or bovine albumin). Human serum albumin (HSA) is also described in EP 0 303 088 in combination with a carbohydrate (e.g. dextrose, sucrose or maltose) to stabilize a monoclonal antibody for the treatment of Pseudomonas aeruginosa infections.

Human serum albumin (in combination with sugars and amino acids) is also the principle by which monoclonal antibodies are stabilized in EP 0 413 188. In JP 01075433 a mixture of human serum albumin, mannitol and polyethylene glycol is used to stabilize a human monoclonal antibody as a lyophilisate. A further example of the use of macromolecules such as e.g. polyethylene glycols and protecting proteins such as human serum albumins to stabilize gamma-globulins during lyophilization is shown in WO 84/00890.

In WO 93/01835 Hagiwara et al. describe the stabilization of a human monoclonal antibody by lyophilization with mannitol and glycine in a solution containing sodium chloride and phosphate buffer. Stable preparations are obtained with regard to freezing, lyophilization and reconstitution.

Draber et al. (J. Immun. Methods, 1995, 181:37-43) were able to produce a stable formulation of monoclonal IgM antibodies from the mouse at 4° C. by the addition of trehalose alone and in combination with polyethylene glycol 8,000. However, the antibodies are only stable for 14 days at 50° C. Using other monosaccharides or disaccharides alone such as e.g. sucrose, maltose, lactose or galactose it is not possible to stabilize these antibodies.

A monoclonal antibody from the mouse is converted into a stable lyophilisate in WO 89/11297 using a carbohydrate (maltose) and a buffer in the acid range (acetate buffer). In this case a disadvantage is the limitation to buffering in an acid range.

Polymeric gelatin as a freezing protectant and stabilizer in a lyophilisate is used in WO 92/15 331. The stabilization is also achieved in combination with a carboxylic acid (e.g. citric acid) or a salt thereof as well as with a primary, secondary or tertiary alcohol or an amino acid in a pH range of 6.8 to 8.1.

In a whole series of the aforementioned publications pharmaceutical additives or auxiliary substances are proposed as stabilizers which are not acceptable from a medical point of view. Hence polymers (such as PEG or gelatin) and proteins (such as serum albumins) pose a certain risk due to their origin and their physico-chemical properties and can trigger allergic reactions even to the point of an anaphylactic shock. Proteins of human or animal origin as well as proteins obtained from cell cultures carry the residual risk of viral contaminations. However, other protein-like contaminations which are difficult to detect analytically can cause immunological reactions in humans due to their properties.

The addition of polymeric compounds such as e.g. polyethylene glycols (PEG) or gelatin can lead to an accumulation in the body with potentially toxic side-effects if there is no biodegradation. Polymers may also have antigenic properties depending on their molar mass. Also it is difficult to ensure the purity of polymers due to the catalysts used in their production or the presence of monomers and other polymer fragments. The use of polymers in pharmaceutical forms of administration, especially in drug forms that can be administered subcutaneously, should be avoided if another type of stabilization is possible.

In contrast the use of sugars alone without other additives does not always ensure an adequate protective effect when the antibodies are lyophilized.

Hence the object of the invention was to provide a stable pharmaceutical preparation of monoclonal or polyclonal antibodies that is essentially free of the above-mentioned polymers or proteinaceous pharmaceutical auxiliary substances. This applies particularly to those antibodies which are labile towards freezing and thawing processes or towards multiple freezing and thawing processes.

Surprisingly it was found that stable pharmaceutical lyophilisates of monoclonal or polyclonal antibodies are obtained if these contain sugar or amino sugar, an amino acid and a surfactant as additives. The lyophilisates are preferably composed of a) the antibody, b) a sugar or amino sugar, c) an amino acid, d) a buffer for adjusting the pH value and e) a surfactant. Those lyophilisates are particularly preferred which only contain a single or two different amino acids.

These preparations are physiologically well tolerated, have a relatively simple composition and can be dosed exactly. In addition they are stable i.e. they exhibit no detectable degradation products or protein aggregates when subjected to multiple freezing and thawing processes as well as on longer storage. The lyophilisates can even be stored without stability problems at refrigerator temperature (4-12° C.) or even at room temperature (18-23° C.) over a time period of at least three months, preferably at least six months and in particular of at least one to two years. Furthermore they are also stable when stored at higher temperatures (for example up to 30° C.). The storage stability is for example exhibited by the fact that during the said storage period only a very small number of particles can be detected when the lyophilisates are reconstituted in the containers with water for injection purposes or with isotonic solutions. In particular the containers have fewer than 6000 particles with a particle size of more than 10 μm and/or less than 600 particles with a particle size of more than 25 μm. The solutions prepared in this manner are stable over a time period of about up to five days, preferably up to three days.

The fact that the preparations protect against freezing due to the selected combination of additives is particularly advantageous. Hence, in particular this enables a lyophilization at temperatures down to −45° C. without impairing the stability of the antibodies. In addition the lyophilisates containing the combination of additives according to the invention are also stable for a long period and during storage even at relatively high temperatures. Especially compared to conventional formulations, they exhibit no particle formation after reconstitution with water, i.e. the solutions are essentially free of turbidities.

The preparations according to the invention have the additional advantage of being essentially free of protein-like or polymeric auxiliary substances the use of which may be problematic from a medical point of view. Due to the fact that liquid therapeutic or diagnostic agents containing antibodies with a pH value of about 5 to 8, preferably with a pH value of 6.0-7.4 (pH value of blood 7.2-7.4) can now be prepared by dissolving lyophilisates, they have the additional advantage of being well-tolerated and can be administered substantially free of pain. This is above all important for subcutaneous administration since in this case intolerances develop more easily than when administered intravenously.

The formulations according to the invention can in general be produced in clinically relevant concentration ranges of the antibody for example of up to 20 mg/ml preferably up to 10 mg/ml. Preferred concentration ranges are concentrations above 0.01 mg/ml in particular above 0.05 and 0.1 mg/ml. In particular concentration ranges of 0.05-10 mg/ml or 0.1-5 mg/ml for example about 5, 8 or 10 mg/ml are used. The injection volumes of the solutions used are less than 2 ml preferably about 1 ml in the case of subcutaneous or intravenous injections. Small injection volumes are particularly advantageous for subcutaneous administration since they only cause slight mechanical irritation in the subcutaneous tissue. Basically the solutions are also directly suitable as additives to infusion solutions or as infusion solutions. If they are used as additives to infusion solutions the concentration of the antibodies is at higher levels, for example up to 10 mg/ml. These concentrated solutions of the antibodies are then added to conventional infusion solutions so that the concentration of the antibody in the infusion solution to be administered is in the therapeutically relevant range. This range is normally 0.001-0.5 mg/ml.

The pharmaceutical single forms of administration can either be present as ready-to-use infusion solutions or injection solutions or also as lyophilisates. If the pharmaceutical preparations are used in the form of lyophilisates, the single dose containers, for example glass ampoules with a volume of 10 ml, contain the antibody in amounts of 0.1-500 mg, preferably 10-100 mg depending on the respective therapeutically relevant dose of the antibody. The lyophilisate optionally contains additional conventional pharmaceutical auxiliary substances. The lyophilisate is dissolved with an appropriate amount of reconstitution solution and can then either be used directly as an injection solution or as an additive to an infusion solution. If it is used as an additive to infusion solutions, the lyophilisate is usually dissolved with about 10 ml of a reconstitution solution and added to a physiological saline solution (0.9% NaCl) of 250 ml. The resulting infusion solution is then usually administered to the patient within about 30 minutes.

The sugars used according to the invention can be monosaccharides, disaccharides or trisaccharides. Glucose, mannose, galactose, fructose and sorbose come into consideration as monosaccharides. Sucrose, lactose, maltose or trehalose come into consideration as disaccharides. Raffinose is preferably used as the trisaccharide. According to the invention sucrose, lactose, maltose, raffinose or trehalose are especially preferably used. Instead of maltose it is also possible to use the stereoisomeric disaccharides cellobiose, gentiobiose or isomaltose.

Those monosaccharides are generally referred to and used as amino sugars which have an amino ($-NH_2$, $-NHR$, $-NR_2$) or an acylated amino group ($-NH-CO-R$) instead of a hydroxy group. For this glucosamine, N-methylglucosamine, galactosamine and neuraminic acid are particularly preferred according to the invention. The sugar content or amino sugar content is for example up to 2000 mg, preferably up to 1000 mg especially up to 800 or up to 500 mg per single form of administration. Amounts of more than 10, 50 or 100 mg come for example into consideration as the lower limit for the sugar content. Preferred ranges are 200-1000 mg, especially 400-800 mg. The stated quantities per single form of administration refer to single forms of administration which are marketed as lyophilisates. Such lyophilisates are preferably filled into injection bottles with a volume of 10 ml. After dissolution of the lyophilisates with a reconstitution solution of 10 ml, liquid forms of administration are obtained which can be administered directly. The sugar concentration in these injection solutions is up to 200 mg/ml, preferably up to 100 mg/ml based on the amounts stated above of the sugars used.

The amino acids used according to the invention can be basic amino acids such as arginine, lysine, histidine, ornithine etc., the amino acids preferably being used in the form of inorganic salts thereof (preferably in the form of phosphoric acid salts i.e. as amino acid phosphates). If free amino acids are used, the desired pH value is adjusted by adding a suitable physiologically tolerated buffer substance such as e.g. an inorganic acid in particular phosphoric acid, sulphuric acid, acetic acid, formic acid or salts thereof. In this case the use of phosphates has the particular advantage that particularly stable lyophilisates are obtained. It has proven to be advantageous when the preparations are essentially free of organic acids such as e.g. malic acid, tartaric acid, citric acid, succinic acid, fumaric acid, etc. or the corresponding anions (malates, oxalates, citrates, succinates, fumarates, etc.) are not present.

Preferred amino acids are arginine, lysine or ornithine. In addition it is also possible to use acidic amino acids such as glutamic acid and aspartic acid or neutral amino acids such as e.g. isoleucine, leucine and alanine or aromatic amino acids such as e.g. phenylalanine, tyrosine or tryptophan. The amino acid content in the aqueous preparations according to the invention is up to 100 mg/ml, preferably up to 50 mg/ml or up to 30 mg/ml. The lower limit may for example be concentrations above 1, 5 or 10 mg/ml. Preferred concentrations are for example in the range of 3-30 mg/ml or 10-25 mg/ml.

If the corresponding forms of administration are marketed as lyophilisates, these lyophilisates are preferably made available in injection bottles (volumes of for example 10 ml). Such single forms of administration contain the amino acids in amounts of up to 1000 mg, preferably up to 500 mg or up to 300 mg.

Surfactants which come into consideration are all surfactants that are usually used in pharmaceutical preparations preferably polysorbates and polyoxyethylene-polyoxypropylene polymers such as e.g. Tween®. Low amounts of surfactant of 0.05 to 0.5 mg/ml preferably 0.1 mg/ml are sufficient to stabilize the antibodies. In the above-mentioned single forms of administration the amount of surfactants is 0.5-5 mg in the case of a lyophilisate that is filled into an injection bottle of 10 ml.

The stabilization of antibodies achieved by the said additives relates in principle to all known monoclonal and polyclonal antibodies and their Fab fragments. Humanized antibodies and modified antibodies (cf. e.g. U.S. Pat. No. 5,624, 821; EP 0 592 106; PCT/EP96/00098) are preferably used. The molecular weight of the antibodies is 50 kDa-200 kDa per monomer unit, in particular the molecular weight is about 80-150 kDa. In particular antibodies to the hepatitis B virus (cf. WO 94/11495), to AIDS viruses, cytomegalo viruses, meningoencephalitis viruses (FSME), rubella viruses, measles viruses, rabies pathogens, Pseudomonas aeruginosa bacteria, varicella-zoster viruses, tetanus pathogens, van Willebrandt factor (cf. WO 96/17078), NGFR (nerve growth factor receptor), PDGFR (platelet derived growth factor receptor: Shulman, Sauer, Jackman, Chang, Landolfi, J. Biol. Chem. 1997, 272(28): 17400-4), selectin, in particular E-selectin, L-selectin (cf. Takashi et al., Proc. Natl. Acad. Sci. USA 1990, 87: 2244-2248; WO 94/12215) or P-selectin; integrins or diphtheria pathogens can be stabilized according to the invention. The antibody concentration can preferably be up to 8 mg/ml. It is preferably for example 0.05-2 mg/ml. The amount of antibody in the single form of administration, for example in a lyophilisate in an injection bottle of 10 ml, is up to 100 mg preferably up to 80 mg, 50 mg, 20 mg or 10 mg. The concentration of the antibodies after reconstitution of the lyophilisates with a volume of 10 ml is in the range of 1-10 mg/ml, preferably at 5-8 mg/ml.

In addition to the said additives, sugar, amino acid and surfactant, the lyophilisates according to the invention can contain physiologically tolerated auxiliary substances from the group comprising acids, bases, buffers or isotonizing agents to adjust the pH value to 5 to 8, preferably 6.0 to 7.4. The buffer capacity of the preparations is adjusted such that when the lyophilisates are dissolved with standard reconstitution solutions such as for example water for injection purposes the buffer concentration is in the range between 10-20 mmol/l preferably at about 15 mmol/l.

The order of addition of the various auxiliary substances or of the antibody is largely independent of the production process and is up to the judgement of a person skilled in the art. The desired pH value of the solution is adjusted by adding bases such as for example alkali hydroxides, alkaline earth hydroxides or ammonium hydroxide. Sodium hydroxide is preferably used for this. The desired pH value can in principle be adjusted by adding basic solutions. In this sense salts of strong bases with weak acids are generally suitable such as sodium acetate, sodium citrate, di-sodium or sodium dihydrogen phosphate or sodium carbonate. If the pharmaceutical solution of auxiliary substances has a basic pH value it is adjusted by titration with an acid until the desired pH range has been reached. Physiologically tolerated inorganic or organic acids come into consideration as acids such as for example hydrochloric acid, phosphoric acid, acetic acid, citric acid or conventional solutions of substances which have an acidic pH value. In this sense preferred substances are salts of strong acids with weak bases such as e.g. sodium dihydrogen phosphate or disodium hydrogen phosphate. The pH value of the solution is preferably adjusted with phosphoric acid or an aqueous sodium hydroxide solution.

In order to produce well-tolerated parenteral drug forms it is expedient to add isotonizing auxiliary substances if isotonicity cannot be already achieved by the osmotic properties of the antibody and the additives used for stabilization. Non-ionized well-tolerated auxiliary substances are used above all for this. Salts such as NaCl should, however, only be added in small amounts, in particular a value of 30 mmol/l in the final injection or infusion solution for administration should not be exceeded.

In addition the pharmaceutical preparations can contain further common auxiliary substances or additives. Antioxidants such as for example glutathione or ascorbic acid or similar substances can be added.

For the production of the lyophilisates the aqueous pharmaceutical solutions which contain the antibody are firstly produced. A buffered antibody solution containing sodium chloride is preferably prepared. This antibody solution is admixed with an aqueous solution containing the additives sugar, amino acid and surfactant during which the pH value is adjusted with an acid or base to 5 to 8. Phosphoric acid or phosphate salts and sodium chloride are added in such amounts that the previously defined concentrations are obtained. Subsequently it is sterilized by filtration and the solution prepared in this manner is lyophilized.

The invention also enables unstable aqueous solutions containing antibodies that are sensitive to freezing to be also converted by means of freeze-drying into stable preparations that are also stable at high temperatures without impairing the quality.

A further advantage of the lyophilisates according to the invention is that, in addition to avoiding damage to the antibodies during freezing, they also exhibit no reduction in the antibody content and no aggregate formation or flocculation even after a long-term storage at 50° C. They are thus stable with regard to antibody content and purity. The formation of particles is prevented which is exhibited by the low values for turbidity after reconstitution of the lyophilisates with water for injection purposes.

The invention is elucidated in more detail in the following on the basis of examples of application.

Examples 1 to 10 show in which manner the lyophilisates according to the invention can be formulated, produced and examined with regard to antibody stability.

Comparative experiments without auxiliary substances or with sucrose alone or with mannitol as a substitute for the sugar component or with the amino acid component alone or only the sugar or amino acid component without the surfactant show that the choice of the combination of additives according to the invention is essential for achieving a stable formulation. Sucrose alone, amino acid alone or both components without surfactant lead to unstable formulations.

The formulations according to the invention are insensitive to freezing and it is possible to completely omit polymers or proteins that are regarded as being toxic such as polyethylene glycols, gelatin, serum albumins. In the case of the surfactants only relatively small amounts of physiologically well-tolerated surfactants are present.

The antibody to HBV used in the following application examples is a recombinant human monoclonal antibody (MAB) from a murine cell. It has a molecular weight of about 147 kDa and is directed towards the hepatitis B surface antigen (HBsAg) of the hepatitis B virus. The monoclonal antibody recognizes the a-determinant of the HBsAg which is constant in almost all known variants of the virus. This antibody can for example be used for the following medical indications: treatment of chronic hepatitis for which there has previously not yet been a satisfactory treatment method; treatment of passive immunoprophylaxis in HBsAg-positive liver transplant patients. In central and northern Europe and the USA up to 2% of the population are carriers of the hepatitis B virus, in southern Europe up to 3%, in Africa and the Far East it is 10-15%. A consequence of this chronic infection is that the risk of developing hepatocellular carcinoma is increased by 100-fold, 40% of the virus carriers die as a result of this infection.

Antibodies to L-selectin, the NGF receptor or the PDGF receptor can be preferably used as antibodies within the sense of the invention.

Example 1 shows the properties of an aqueous solution of a monoclonal antibody to hepatitis B virus (MAB HBV; INN name: Tuvirumab) containing phosphate buffer and sodium chloride at pH=5, pH=6.5 and pH=8 after freezing and thawing. It shows that freezing and thawing damages the monoclonal antibody.

Example 2 demonstrates the possibility of stabilizing a preparation according to the invention with sucrose or maltose or an amino sugar (N-methylglucosamine or galactosamine) and arginine phosphate and Tween 20 with a concentration of the antibody of 2 mg/ml i.e. 2 mg in the lyophilisate.

The same preparation as in example 2 is shown in example 2a except that the antibody concentration is 8 mg/ml. It can be seen from examples 2 and 2a that the combination of the said auxiliary substances not only avoids damage to the antibody during freezing but also has a positive influence on the stability during long-term storage.

Example 3 elucidates the necessity of amino acids and surfactant in the preparation according to the invention. The use of sucrose as a builder alone leads to an unstable lyophilisate.

Example 4 describes variations of the amino acid component. It turns out that variation of the basic amino acids in the form of arginine or ornithine as well as the substitution of the basic amino acid by a neutral amino acid such as e.g. by leucine or by an acidic amino acid such as e.g. aspartic acid leads to a storage-stable preparation.

In example 5 the lyophilisation of a formulation containing sucrose, arginine and Tween 20 as well as phosphate buffer and sodium chloride is compared at various pH values (pH 5, pH 6.5 and pH 8). The data obtained show that it is possible to lyophilize within this pH range without impairing the stability.

If the said surfactant Tween 20 is replaced by a representative of the surface-active class of compounds polyoxyethylene-polyoxypropylene polymers (commercial name Pluronic®) as in example 6 this also results in an adequate stability of the preparation according to the invention.

Example 7 demonstrates the instability of a formulation containing mannitol as the builder as a substitute for sucrose, maltose or the amino sugar (see example 2).

If the sugar and the surfactant are omitted in the formulation the preparation becomes unstable as shown in example 8.

Although a combination of sugar (e.g. sucrose) and amino acids without surfactant in example 9 yields good results with regard to the parameters content and aggregates, the turbidity is, however, substantially increased compared to the formulations according to the invention containing sugar, amino acid and surfactant.

Example 10 shows that other monoclonal antibodies can also be stabilized with a combination of the sugar, amino acid and surfactant. The antibody anti-L-selectin is for example stable at a concentration of 7 mg in the lyophilisate. The lyophilization is carried out starting with a volume of 1 ml of an aqueous solution.

Investigative Methods to Determine Stability

The lyophilized preparations were stored under defined storage conditions in the absence of light and subsequently analysed. The following test methods were used for the analyses.

OD280: Optical density at 280 nm. Photometric determination of the protein content, the UV absorbance is due to side chain chromophores such as tryptophan tyrosine and phenylalanine residues. Specification: 95-105%.

SE-HPLC: Size-exclusion high performance chromatography to determine aggregates. Specification: max. 2%.

Measurement of turbidity: After reconstituting the lyophilisate the undiluted antibody solution was measured in a suitable turbidity photometer. Specification: max. 6 turbidity units.

EXAMPLE 1

An aqueous stock solution of the MAB to HBV described above containing phosphate buffer and sodium chloride is prepared and examined. The concentration of the MAB is about 15 mg/ml.

Table 1a shows on the one hand the liability to freezing of the monoclonal antibody solution at various pH values at −20° C. which already results in a decrease of the protein content after 4 weeks to 92.1 and 94.2 and 94.0%. A decrease of the protein content is also observed on storage at 25° C. Under the storage conditions 4-8° C. in a refrigerator the antibody is adequately stable over 9 months.

Tables 1b-1d show the stability data of the monoclonal antibody solution prepared at pH values 5, 6.5 and 8 at −20° C., 4-8° C. and 25° C. This also shows that only a storage at 4-8° C. is acceptable.

TABLE 1a

Change of the antibody content in the solution of active substance (10 mM phosphate buffer, 30 mM sodium chloride, water for injection purposes)

| | pH 5 | | | pH 6.5 | | | pH 8 | | |
|---|---|---|---|---|---|---|---|---|---|
| Time | −20° C. | 4-8° C. | 25° C. | −20° C. | 4-8° C. | 25° C. | −20° C. | 4-8° C. | 25° C. |
| start | | >99 | | | >99 | | | >99 | |
| 4 weeks | 92.1 | >99 | >99 | 94.2 | >99 | >99 | 94.0 | >99 | >99 |
| 13 weeks | 78.9 | >99 | 97.2 | 81.2 | >99 | 98.1 | 77.8 | >99 | 96.1 |
| 6 months | 61.2 | >99 | 94.1 | 69.9 | >99 | 94.4 | 65.8 | >99 | 91.9 |
| 9 months | 47.8 | >99 | 88.7 | 55.6 | >99 | 90.2 | 51.0 | >99 | 84.3 |

All data in %. The protein was determined by measuring the absorbance at 280 nm (OD 280).

TABLE 1b

Aggregate formation and turbidity values for the active substance solution of antibody, pH = 5

| | −20° C. | | 4-8° C. | | 25° C. | |
|---|---|---|---|---|---|---|
| Times | aggregates | turbidity | aggregates | turbidity | aggregates | turbidity |
| start | n.d. | 1.5 | n.d. | 1.5 | n.d. | 1.5 |
| 4 weeks | aggregates | floccul. | n.d. | 1.5 | 0.7% | 1.5 |
| 13 weeks | aggregates | floccul. | 0.2% | 1.8 | 1.9% | 1.8 |
| 6 months | aggregates | floccul. | 0.3% | 1.9 | aggregates | 9.9 |
| 9 months | aggregates | floccul. | 0.6% | 2.1 | aggregates | 10.9 | n.d. = not detectable

TABLE 1c

Aggregate formation and turbidity values for the active substance solution of antibody, pH = 6.5

| | −20° C. | | 4-8° C. | | 25° C. | |
|---|---|---|---|---|---|---|
| Times | aggregates | turbidity | aggregates | turbidity | aggregates | turbidity |
| start | n.d. | 1.2 | n.d. | 1.2 | n.d. | 1.2 |
| 4 weeks | aggregates | floccul. | n.d. | 1.3 | 0.5% | 1.4 |
| 13 weeks | aggregates | floccul. | 0.2% | 1.4 | 1.8% | 1.7 |
| 6 months | aggregates | floccul. | 0.3% | 1.9 | 4.9% | floccul. |
| 9 months | aggregates | floccul. | 0.6% | 2.1 | 9.3% | floccul. |

TABLE 1d

Aggregate formation and turbidity values for the active substance solution of antibody, pH = 8

| | −20° C. | | 4-8° C. | | 25° C. | |
|---|---|---|---|---|---|---|
| Times | aggregates | turbidity | aggregates | turbidity | aggregates | turbidity |
| start | n.d. | 1.4 | n.d. | 1.4 | n.d. | 1.4 |
| 4 weeks | 2.0% | floccul. | 0.3% | 1.5 | 0.74% | 1.7 |
| 13 weeks | 2.8% | floccul. | 0.5% | 1.8 | 1.95% | 2.1 |
| 6 months | 3.7% | floccul. | 0.6% | 1.9 | 3.0% | floccul. |
| 9 months | 5.4% | floccul. | 0.8% | 2.1 | 4.3% | floccul. |

Aggregates in % using SE-HPLC, turbidity in turbidity units (turbidity) using a turbidity photometer.

EXAMPLE 2

A solution of the monoclonal antibody to HBV according to example 1 was added to aqueous solutions of the following sugars or amino sugars: sucrose (formulation 1), maltose (formulation 2) and N-methylglucosamine (formulation 3) containing arginine phosphate buffer and Tween 20 as the surfactant. The formulation is listed in example 2a. The final concentration of the MAB is 2 mg/ml. After adjusting the pH value with phosphoric acid to 6.5, the solutions were sterilized by filtration (0.22 μm membrane filter) and filled into sterilized and depyrogenized injection bottles made of glass (hydrolytic class I) (filling volumes 1 ml) and lyophilized. After lyophilization the injection bottles were aerated with nitrogen, sealed automatically with stoppers in the freeze drying chamber and subsequently flanged.

The flanged injection bottles were stored in the absence of light for 4 to 13 weeks at various temperatures. After these periods the stability of the lyophilisates was examined with the described methods of examination.

TABLE 2 a: Storage at 25° C.

| | Storage 4 weeks at 25° C. | | | Storage 13 weeks at 25° C. | | |
|---|---|---|---|---|---|---|
| | I | II | III | I | II | III |
| form. 1 sucrose | 100 | n.d. | 1.7 | 100 | n.d. | 1.6 |
| form. 2 maltose | 100 | n.d. | 1.6 | 100 | n.d. | 1.8 |
| form. 3 N-methyl-glucosamine | 100 | n.d. | 1.8 | 100 | n.d. | 1.5 |

TABLE 2-continued b: Storage at 50° C.

|  | Storage 4 weeks at 50° C. | | | Storage 13 weeks at 50° C. | | |
| --- | --- | --- | --- | --- | --- | --- |
|  | I | II | III | I | II | III |
| form. 1 sucrose | >99 | n.d. | 2.0 | >99 | n.d. | 2.0 |
| form. 2 maltose | >99 | n.d. | 1.9 | >99 | n.d. | 2.1 |
| form. 3 N-methyl-glucosamine | >99 | n.d. | 1.7 | >99 | n.d. | 2.0 |

Legend:
I protein content in % with OD 280
II aggregates in % with SE-HPLC
III turbidity of the reconstituted solution in turbidity units (dimensionless number)
n.d. not detectable (used in the same way in all further tables)

EXAMPLE 2a

In example 2a the formulation 1 from example 2 is prepared with 8 mg/ml antibody (=formulation 1a). It turns out that higher concentrations of up to 8 mg/1 ml antibody are adequately stable in this formulation.
Compositions of Formulations 1 and 1a:

|  | Formulation 1 | Formulation 1a |
| --- | --- | --- |
| MAB HBV | 2.0 mg | 8.0 mg |
| phosphate buffer | 15 mM | 15 mM |
| sodium chloride | 30 mM | 30 mM |
| sucrose | 68.0 mg | 58.0 mg |
| arginine | 10.0 mg | 10.0 mg |
| phosphoric acid | ad pH 6.5 | ad pH 6.5 |
| Tween 20 | 0.1 mg | 0.1 mg |
| water for injection purposes | ad 1.0 ml | ad 1.0 ml |

TABLE 3 a: Stability data for formulation 1 and formulation 1a at 25° C.

|  | Storage 4 weeks at 25° C. | | | Storage 13 weeks at 25° C. | | |
| --- | --- | --- | --- | --- | --- | --- |
|  | I | II | III | I | II | III |
| form. 1: 2 mg/1 ml | 100 | n.d. | 1.7 | 100 | n.d. | 1.6 |
| form. 1a: 8 mg/1 ml | >99 | n.d. | 4.8 | >99 | n.d. | 4.7 | b: Stability data for formulations 1 and 1a at 50° C.

|  | Storage 4 weeks at 50° C. | | | Storage 13 weeks at 50° C. | | |
| --- | --- | --- | --- | --- | --- | --- |
|  | I | II | III | I | II | III |
| form. 1: 2 mg/1 ml | >99 | n.d. | 2.0 | >99 | n.d. | 2.0 |
| form. 1a: 8 mg/1 ml | >99 | n.d. | 4.7 | >99 | n.d. | 5.5 |

I protein content in % with OD 280
II aggregates in % with SE-HPLC
III turbidity of the reconstituted solution in turbidity units (dimensionless number)

EXAMPLE 3

Comparison of formulations 1 and 4. Formulation 4 only contains sucrose as the builder and no arginine phosphate and no Tween 20. Formulation 4 is unstable.

|  | Formulation 1 | Formulation 4 |
| --- | --- | --- |
| MAB HBV | 2.0 mg | 2.0 mg |
| phosphate buffer | 15 mM | 15 mM |
| sodium chloride | 30 mM | 30 mM |
| sucrose | 68.0 mg | 68.0 mg |
| arginine | 10.0 mg | — |
| phosphoric acid or NaOH | ad pH 6.5 | ad pH 6.5 |
| Tween 20 | 0.1 mg | — |
| water for injection purposes | ad 1.0 ml | ad 1.0 ml |

TABLE 4 a: Storage at 25° C.

|  | Storage 4 weeks at 25° C. | | | Storage 13 weeks at 25° C. | | |
| --- | --- | --- | --- | --- | --- | --- |
|  | I | II | III | I | II | III |
| form. 1: sucrose with arg. phos. and Tween 20 | 100 | n.d. | 1.7 | >99 | n.d. | 1.6 |
| form. 4: sucrose without arg. phos. and Tween 20 | 98.3 | 1.6 | 6.1 | 96.0 | 4.3 | 9.5 | b: Storage at 50° C.:

|  | Storage 4 weeks at 50° C. | | | Storage 13 weeks at 50° C. | | |
| --- | --- | --- | --- | --- | --- | --- |
|  | I | II | III | I | II | III |
| form. 1: sucrose with arg. phos. and Tween 20 | 100 | n.d. | 2.0 | >99 | n.d. | 2.0 |
| form. 4: sucrose without arg. phos. and Tween 20 | 96.0 | 4.2 | 8.5 | 89.8 | 10.1 | 10.9 |

Legend:
I protein content in % with OD 280
II aggregates in % with SE-HPLC turbidity of the reconstituted solution in turbidity units (dimensionless number)
III turbidity of the reconstituted solution in turbidity units (dimensionless number)

EXAMPLE 4

Variation of the amino acid component of the formulation. Formulations with basic, acidic and neutral amino acids are stable.
Composition of the Formulations:

| MAB HBV | 2.0 mg |
| --- | --- |
| phosphate buffer | 15 mM |
| sodium chloride | 30 mM |
| sucrose | 35-70 mg |
| amino acid | variable |
| phosphoric acid or NaOH | ad pH 6.5 |
| Tween 20 | 0.1 mg |
| water for injection purposes | ad 1.0 ml |

TABLE 5

| | Amino acid |
| --- | --- |
| formulation 1 | arginine (basic) |
| formulation 5 | ornithine (basic) |
| formulation 6 | leucine (neutral) |
| formulation 7 | aspartic acid (acidic) |

The pH value is adjusted by phosphoric acid or hydroxide solution.

Tables 6a-d

Examination results of formulations 1, 5, 6, 7 after storage for 4 and 13 weeks.

TABLE 6a a) Formulation 1 (arginine):

|  | Storage period 25° C. 4 weeks | Storage 50° C. | Storage period 25° C. 13 weeks | Storage 50° C. |
|---|---|---|---|---|
| protein content % (OD 280) | 100 | >99 | 100 | >99 |
| aggregates % (SE-HPLC) | n.d. | n.d. | n.d. | n.d. |
| turbidity | 1.7 | 2.0 | 1.6 | 2.0 |

TABLE 6b b) formulation 5 (ornithine):

|  | Storage period 25° C. 4 weeks | Storage 50° C. | Storage period 25° C. 13 weeks | Storage 50° C. |
|---|---|---|---|---|
| protein content % (OD 280) | >99 | >98 | >98 | >98 |
| aggregates % (SE-HPLC) | n.d. | n.d. | n.d. | n.d. |
| turbidity | 1.9 | 1.9 | 2.0 | 2.1 |

TABLE 6c c) formulation 6 (leucine):

|  | Storage period 25° C. 4 weeks | Storage 50° C. | Storage period 25° C. 13 weeks | Storage 50° C. |
|---|---|---|---|---|
| protein content % (OD 280) | >98 | >98 | >98 | >98 |
| aggregates % (SE-HPLC) | n.d. | n.d. | 0.1 | 0.1 |
| turbidity | 2.2 | 2.4 | 2.8 | 2.7 |

TABLE 6d d) formulation 7 (aspartic acid):

|  | Storage period 25° C. 4 weeks | Storage 50° C. | Storage period 25° C. 13 weeks | Storage 50° C. |
|---|---|---|---|---|
| protein content % (OD 280) | >98 | >98 | >98 | >98 |
| aggregates % (SE-HPLC) | n.d. | n.d. | 0.1 | 0.1 |
| turbidity | 2.7 | 2.7 | 3.4 | 4.0 |

EXAMPLE 5

Example 5 contains formulation 1 at various pH values, the lyophilisates are prepared as described in example 2, the pH of the solution of auxiliary substances and of the product solution was adjusted before lyophilisation with 85% phosphoric acid.

Formulation:

| MAB HBV | 2.0 mg |
|---|---|
| phosphate buffer | 15 mM |
| sodium chloride | 30 mM |
| sucrose | 68 mg |
| arginine | 10 mg |
| phosphoric acid | ad pH 5; 6.5; 8 |
| Tween 20 | 0.1 mg |
| water for injection purposes | ad 1.0 ml |

The lyophilisates were prepared with the pH values shown in table 7.

After flanging the injection bottles these were stored in the absence of light under defined temperature conditions. After storage periods of 4 weeks and 13 weeks the samples were analysed (protein content in %: OD 280, aggregates in %: SE-HPLC, turbidity). The formulation was stable at all pH values.

TABLE 7

|  | pH |
|---|---|
| formulation 8 | 5 |
| formulation 9 (ident. with 1) | 6.5 |
| formulation 10 | 8 |

TABLE 8 a: Storage at 25° C.

|  | Storage 4 weeks at 25° C. | | | Storage 13 weeks at 25° C. | | |
|---|---|---|---|---|---|---|
|  | I | II | III | I | II | III |
| formulation 8 | 100 | n.d. | 1.9 | >99 | n.d. | 2.3 |
| formulation 9 (=1) | 100 | n.d. | 1.7 | 100 | n.d. | 1.6 |
| formulation 10 | >99 | n.d. | 2.3 | >99 | n.d. | 2.6 | b: Storage at 50° C.

|  | Storage 13 weeks at 50° C. | | | Storage 13 weeks at 50° C. | | |
|---|---|---|---|---|---|---|
|  | I | II | III | I | II | III |
| formulation 8 | >99 | n.d. | 2.2 | >99 | n.d. | 2.3 |
| formulation 9 (=1) | >99 | n.d. | 2.0 | >99 | n.d. | 2.0 |
| formulation 10 | >98 | n.d. | 2.5 | >98 | n.d. | 2.6 |

Legend:
I protein content in % with OD 280
II aggregates in % with SE-HPLC
III turbidity of the reconstituted solution in turbidity units (dimensionless number)

EXAMPLE 6

The formulation described in the following containing the surfactant Pluronic F 68 instead of Tween 20 was prepared as described above.

The storage and examination of stability was carried out in an analogous manner to that of the other examples.

Formulation 11:

| MAB HBV | 2.0 mg |
|---|---|
| phosphate buffer | 15 mM |
| sodium chloride | 30 mM |
| sucrose | 48.0 mg |
| arginine | 10.0 mg |
| phosphoric acid | ad pH 6.5 |
| Pluronic F 68 | 0.1 mg |
| water for injection purposes | ad 1.0 ml |

Formulation 1 is chosen as a comparison and is identical to formulation 11 except for Tween 20 instead of Pluronic F 68. Both formulations were stable.

TABLE 9

Stability data of the formulation containing the surfactants Pluronic F 68 and Tween 20.

| | formulation 11 | | | | formulation 1 | | | |
| --- | --- | --- | --- | --- | --- | --- | --- | --- |
| | storage period 4 weeks | | storage period 13 weeks | | storage period 4 weeks | | storage period 13 weeks | |
| | 25° C. | 50° C. | 25° C. | 50° C. | 25° C. | 50° C. | 25° C. | 50° C. |
| protein content % (OD 280) | >98 | >98 | >98 | >98 | 100 | >99 | 100 | >99 |
| aggregates % (SE-HPLC) | n.d. | n.d. | n.d. | n.d. | n.d. | n.d. | n.d. | n.d. |
| turbidity | 1.9 | 1.9 | 2.5 | 2.2 | 1.7 | 2.0 | 1.6 | 2.0 |

EXAMPLE 7

The formulation 12 described in this example essentially corresponds to formulation 1 except that mannitol was used instead of sucrose as a builder. It can be seen that the mannitol formulation is unstable.

Formulation 12:

| | |
| --- | --- |
| MAB HBV | 2.0 mg |
| phosphate buffer | 15 mM |
| sodium chloride | 30 mM |
| mannitol | 25.0 mg |
| arginine | 10.0 mg |
| phosphoric acid | ad pH 6.5 |
| Tween 20 | 0.1 mg |
| water for injection purposes | ad 1.0 ml |

TABLE 10

Stability data of the formulations containing the builder mannitol (formulation 12) and sucrose (formulation 1)

| | formulation 12 | | | | formulation 1 | | | |
| --- | --- | --- | --- | --- | --- | --- | --- | --- |
| | storage period 4 weeks | | storage period 13 weeks | | storage period 4 weeks | | storage period 13 weeks | |
| | 25° C. | 50° C. | 25° C. | 50° C. | 25° C. | 50° C. | 25° C. | 50° C. |
| protein content % (OD 280) | 96.2 | 91.8 | 94.0 | 84.5 | 100 | >99 | 100 | >99 |
| aggregates % (SE-HPLC) | 3.6 | 8.4 | 5.8 | 15.9 | n.d. | n.d. | n.d. | n.d. |
| turbidity | 3.2 | 6.9 | 4.9 | 13.2 | 1.7 | 2.0 | 1.6 | 2.0 |

EXAMPLE 8

Further evidence for the necessity of the combination of sugar, amino acid and surfactant is given by comparing formulation 1 which contains all listed components with formulation 13 composed of antibody, phosphate buffer, sodium chloride and arginine phosphate. The aggregate formation is increased and the turbidity values become worse without sugar and surfactant.

Formulation 13

| | |
| --- | --- |
| MAB HBV | 2.0 mg |
| phosphate buffer | 15 mM |
| sodium chloride | 30 mM |
| arginine | 35.0 mg |
| phosphoric acid | ad pH 6.5 |
| water for injection purposes | ad 1.0 ml |

TABLE 11

Stability data for formulation 13 (without sucrose and Tween 20 only with arginine phosphate as builder) and formulation 1

| | formulation 13 | | | | formulation 1 | | | |
|---|---|---|---|---|---|---|---|---|
| | storage period 4 weeks | | storage period 13 weeks | | storage period 4 weeks | | storage period 13 weeks | |
| | 25° C. | 50° C. | 25° C. | 50° C. | 25° C. | 50° C. | 25° C. | 50° C. |
| protein content % (OD 280) | 97.6 | 94.9 | 95.8 | 89.0 | 100 | >99 | 100 | >99 |
| aggregates % (SE-HPLC) | 2.6 | 4.5 | 4.0 | 10.7 | n.d. | n.d. | n.d. | n.d. |
| turbidity | 2.9 | 4.5 | 3.8 | 12.3 | 1.7 | 2.0 | 1.6 | 2.0 |

EXAMPLE 9

Although a stable formulation is obtained without surfactant (Tween 20) and only with sucrose and arginine, the turbidity values worse (formulation 14).

Formulation 15:

| | |
|---|---|
| MAB HBV | 2.0 mg |
| phosphate buffer | 15 mM |
| sodium chloride | 30 mM |
| sucrose | 68.0 mg |
| arginine | 10.0 mg |
| phosphoric acid | ad pH 6.5 |
| water for injection purposes | ad 1.0 ml |

TABLE 12

Stability data of formulation 14 and formulation 1

| | formulation 14 | | | | formulation 1 | | | |
|---|---|---|---|---|---|---|---|---|
| | storage period 4 weeks | | storage period 13 weeks | | storage period 4 weeks | | storage period 13 weeks | |
| | 25° C. | 50° C. | 25° C. | 50° C. | 25° C. | 50° C. | 25° C. | 50° C. |
| protein content % (OD 280) | >99 | >98 | >98 | >98 | 100 | >99 | 100 | >99 |
| aggregates % (SE-HPLC) | 0.2 | 0.3 | 0.5 | 1.3 | n.d. | n.d. | n.d. | n.d. |
| turbidity | 3.4 | 4.8 | 8.8 | 13.3 | 1.7 | 2.0 | 1.6 | 2.0 |

EXAMPLE 10

The following table shows the components of formulation 15. The antibody used is anti-L-selectin. The data shown in table 13a on the examination of stability show that the formulation used enables an adequate stabilization.

Composition of Formulation 15:

| | Formulation 15 |
|---|---|
| anti-L-selectin | 7.0 mg |
| phosphate buffer | 15 mM |
| sodium chloride | 30 mM |
| sucrose | 68.0 mg |
| arginine | 10.0 mg |
| phosphoric acid | ad pH 6.5 |
| Tween 20 | 0.1 mg |
| water for injection purposes | ad 1.0 ml |

TABLE 13 a: Stability data for formulation 15 at 25° C.

| | Storage 4 weeks at 25° C. | | | Storage 13 weeks at 25° C. | | |
|---|---|---|---|---|---|---|
| | I | II | III | I | II | III |
| form. 15: 7 mg/1 ml | >99 | n.d. | 2.5 | >99 | n.d. | 2.9 |

TABLE 13-continued b: Stability data for formulation 15 at 50° C.

| | Storage 4 weeks at 50° C. | | | Storage 13 weeks at 50° C. | | |
|---|---|---|---|---|---|---|
| | I | II | III | I | II | III |
| form. 15: 7 mg/ml | 99 | n.d. | 4.1 | 99 | n.d. | 5.2 |

I protein content in % with OD 280

II aggregates in % with SE-HPLC

III turbidity of the reconstituted solution in turbidity units (dimensionless number)

EXAMPLE 11

Stabilization of the Antibody Anti-L-NGFR (Anti-L-Nerve-Growth-Factor-Receptor)

Formulation 16:

A lyophilisate with the following formulation (analogous to formulation 1) is prepared:

|  | Formulation 16 |
|---|---|
| anti-L-NGFR | 0.25 mg |
| phosphate buffer | 15 mM |
| sucrose | 75 mg |
| arginine | 10 mg |
| phosphoric acid | ad pH 6.5 |
| Tween 20 | 0.1 mg |
| water for injection purposes | ad 1.0 ml |

The lyophilisate of anti-L-NGFR is prepared analogously to the preparation of the MAB-HBV and anti-L-selectin lyophilisates.

An aqueous solution containing the additives sugar, amino acid and surfactant at pH 5 to 8 is admixed with a solution of the anti-L-NGFR in a phosphate buffer. The phosphate salts are added in such amounts that the previously defined concentrations are obtained. Subsequently it is sterilized by filtration and the solution prepared in this manner is lyophilized. After lyophilisation one obtains an optically perfect lyophilisation cake. The antibody anti-L-NGFR remains stable. After reconstitution of the lyophilisate with water for injection purposes a clear solution is obtained.

The invention claimed is:

1. A process for the production of a lyophilized pharmaceutical preparation of monoclonal or polyclonal antibodies, comprising
    a) producing an aqueous preparation comprising a monoclonal or polyclonal antibody as the active substance at a concentration up to 20 mg/ml, sucrose in a concentration of 35 mg/ml to 75 mg/ml, an amino acid selected from the group consisting of arginine or ornithine in a concentration of 10 mg/ml to 25 mg/ml and a surfactant selected from the group consisting of Tween 20 (Polyethylene glycol sorbitan monolaurate) and Pluronic F68 (polyoxyethylene-polyoxypropylene polymer) in a concentration of 0.1 mg/ml, and
    b) lyophilizing said aqueous preparation.

2. The process according to claim 1, further comprising pharmaceutical auxiliary substances.

3. The process according to claim 1, wherein the monoclonal or polyclonal antibody is present in a concentration of 0.25 mg/ml to 8 mg/ml prior to lyophilization.

* * * * *